United States Patent
Park et al.

(10) Patent No.: US 9,265,832 B2
(45) Date of Patent: Feb. 23, 2016

(54) STABILIZED PEMETREXED FORMULATION

(71) Applicant: CJ HEALTHCARE CORPORATION, Seoul (KR)

(72) Inventors: Young Joon Park, Seoul (KR); Myung Jin Shin, Seoul (KR); Hong Chul Jin, Seongnam-si (KR); Ha Yong Choi, Yongin-si (KR); Nak Hyun Choi, Yongin-si (KR)

(73) Assignee: CJ HEALTHCARE CORPORATION, Seoul (KR)

( * ) Notice: Subject to any disclaimer, the term of this patent is extended or adjusted under 35 U.S.C. 154(b) by 0 days.

(21) Appl. No.: 14/646,615

(22) PCT Filed: Nov. 29, 2013

(86) PCT No.: PCT/KR2013/010967
§ 371 (c)(1),
(2) Date: May 21, 2015

(87) PCT Pub. No.: WO2014/084651
PCT Pub. Date: Jun. 5, 2014

(65) Prior Publication Data
US 2015/0297724 A1    Oct. 22, 2015

(30) Foreign Application Priority Data

Nov. 29, 2012   (KR) .................. 10-2012-0137375

(51) Int. Cl.
*A61K 31/513*   (2006.01)
*A61K 31/519*   (2006.01)
*A61K 47/20*    (2006.01)
*A61K 47/12*    (2006.01)
*A61J 1/05*     (2006.01)

(52) U.S. Cl.
CPC . *A61K 47/20* (2013.01); *A61J 1/05* (2013.01); *A61K 31/519* (2013.01); *A61K 47/12* (2013.01)

(58) Field of Classification Search
CPC ........................ A61K 31/513; A61K 31/519
USPC ........................................ 514/265.1
See application file for complete search history.

(56) References Cited

U.S. PATENT DOCUMENTS

| 5,344,932 A | 9/1994 | Taylor |
| 6,686,365 B2 * | 2/2004 | Riebesehl ............. A61K 45/06 |
| | | 514/262.1 |
| 2009/0181990 A1 | 7/2009 | Patel et al. |

FOREIGN PATENT DOCUMENTS

| EP | 0 434 426 A1 | 6/1991 |
| EP | 1 265 612 B1 | 5/2004 |
| KR | 1020070028331 A | 3/2007 |
| KR | 10-0774366 B1 | 3/2013 |

(Continued)

OTHER PUBLICATIONS

The United States Pharmacopeia, USP 35—The National Formulary, vol. 2, p. 2069 (3 pages) (May 1, 2012).

*Primary Examiner* — Kamal Saeed
*Assistant Examiner* — Janet L Coppins
(74) *Attorney, Agent, or Firm* — Seed IP Law Group PLLC

(57) ABSTRACT

The present invention relates to a stabilized pemetrexed formulation, and more particularly to a stabilized pemetrexed formulation comprising acetylcysteine as antioxidant and a citrate salt as buffer.

6 Claims, 1 Drawing Sheet

(56) References Cited

FOREIGN PATENT DOCUMENTS

| WO | 01/56575 A1 | 8/2001 |
| WO | 2012/015810 A2 | 2/2012 |
| WO | 2012/121523 A2 | 9/2012 |

* cited by examiner

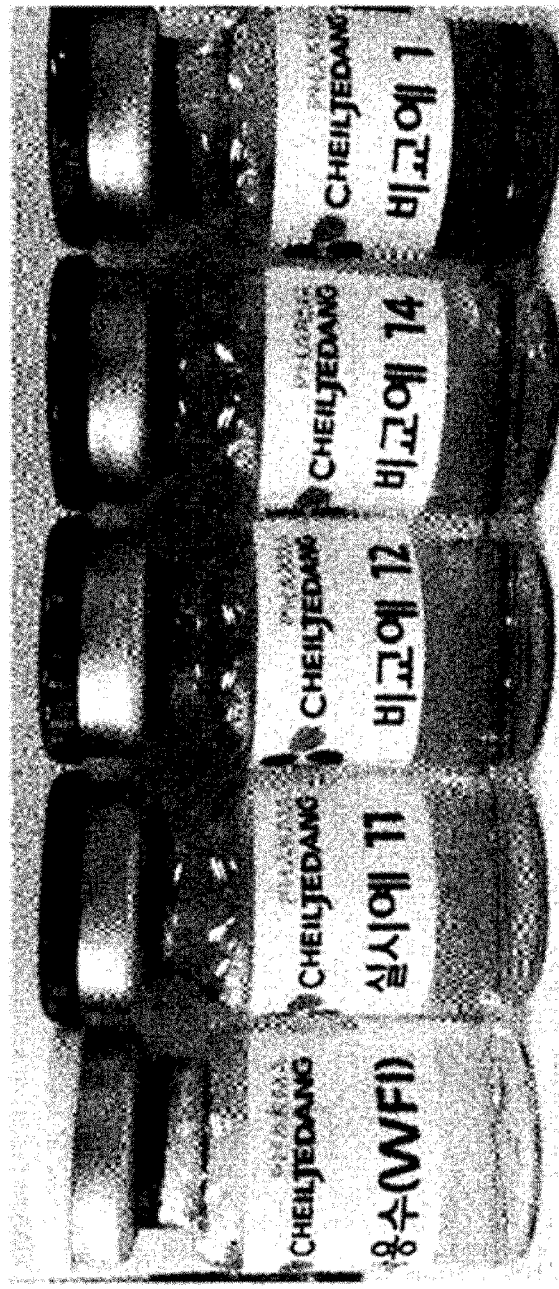

“STABILIZED PEMETREXED FORMULATION

TECHNICAL FIELD

The present invention relates to a stabilized pemetrexed formulation, and more particularly to a stabilized pemetrexed formulation comprising acetylcysteine as antioxidant and a citrate salt as buffer.

BACKGROUND ART

Specific compounds known to have antifolate activity are well known as chemotherapeutic agents for cancer treatment. U.S. Pat. No. 5,344,932 discloses processes for preparing certain substituted pyrrolo[2,3-d]pyrimidin-based antifolate derivatives, including pemetrexed, and European Patent Publication No. 0434426 discloses a series of 4-hydroxypyrrolo [2,3-d]pyrimidine-L-glutamic acid derivatives.

Pemetrexed, a 5-substituted pyrrolo[2,3-d]pyrimidine, is a multitargeted antifolate that exhibits anticancer effects against various cancers, including non-small cell lung cancer, by inhibiting the activity of metabolites that are involved in folate metabolism.

It is known that pemetrexed enters cells through the reduced folate carrier (RFC) that is a major folate transport system, and is then activated by folylpolyglutamate synthetase (FPGS) to form polyglutamate derivatives that target thymidylate synthase (TS) and dihydrofolate reductase (DHFR).

Currently, pemetrexed is marketed under the trade name of Alimta and is used as an agent for treating malignant pleural mesothelioma and non-small cell lung cancer (see Physicians' Desk Reference, $60^{th}$ ed., pp. 1722-1728 (2006)). Alimta is sold in a lyophilized formulation that has to be reconstituted before administration. Specifically, Alimta is sold in a lyophilized powder formulation (100 mg or 500 mg) that needs to be reconstituted with 0.9% sodium chloride solution and finally diluted with 0.9% sodium chloride solution to a final concentration of 0.25 mg/ml, before administration to a patient.

Lyophilized powder formulations are complicated to prepare, and processes for preparing these formulations are very expensive. In addition, lyophilized formulations have the risk of being contaminated with microorganisms upon reconstitution, and pharmacists, physicians, nurses and the like who are involved in the preparation of medicines comprising these formulations are highly likely to be exposed to cell-destroying substances. Thus, in the case of cytotoxic anticancer agents such as pemetrexed, it is required to develop ready-to-use liquid formulations that can be stored for a long period of time, rather than developing lyophilized formulations.

In many cases, the problem of liquid formulations is instability during storage. Due to this instability, a large number of injectable formulations are used in the form of lyophilized formulations that are dissolved immediately before injection. Even in the case of pemetrexed or a pharmaceutically acceptable salt thereof, which has recently been provided in the form of lyophilized formulations, preparation as an aqueous solution formulation causes problems of unknown impurities increased when stored at room temperature for a long period of time. That is, this aqueous solution formulation suffers from a stability problem. Due to this stability problem, pemetrexed or a pharmaceutically acceptable salt thereof is currently used in the form of lyophilized formations in clinical applications.

To overcome the above-described shortcomings, some formulations have been proposed. For example, U.S. Pat. No. 6,686,365 (corresponding to Korean Patent Publication No. 2002-0081293) discloses a stable liquid formulation of pemetrexed, which comprises a therapeutically effective amount of pemetrexed, an effective amount of an antioxidant and a pharmaceutically acceptable excipient, wherein the antioxidant is selected from the group consisting of monothioglycerol, L-cysteine and thioglycolic acid.

However, with respect to the problem of the formulation disclosed in the above patent, it was reported that, when the formulation was stored at 25° C. for a long period of time, precipitation occurred, suggesting that the long-term stability of the formulation for a desired period cannot be guaranteed (PCT International Patent Publication No. WO 2012/ 015810). No liquid pemetrexed formulation stable for long-term storage has been experimentally or commercially realized so far. In fact, the present inventors prepared a pemetrexed-containing liquid formulation using the above-mentioned antioxidant L-cysteine and performed a stability test for the prepared formulation, only to observe several problems, including a change in the appearance, such as discoloration, an increase in impurities, and a decrease in the pH, after 2 weeks under stress testing conditions. In addition, the present inventors prepared pemetrexed-containing liquid formulations using about 60 kinds of stabilizers, including ascorbic acid, sodium thiosulfate, butylated hydroxyanisole, propyl gallate, EDTA, L-methionine, and acetyl cysteine, but these formulations all had insufficient stability.

DISCLOSURE OF INVENTION

Technical Problem

Against the background, the present inventors have conducted extensive studies to overcome the stability problem of liquid pemetrexed formulations, and as a result, have found that, when acetylcysteine as antioxidant and a citrate salt as buffer are used together, a stable pemetrexed formulation with high stability and maintained in a state of a transparent solution without precipitation during storage, in which the formation of pemetrexed isomer impurity and unknown impurities are effectively controlled or inhibited, thereby completing the present invention.

Solution to Problem

It is an object of the present invention to provide a stabilized pemetrexed formulation.

Advantageous Effects of Invention

The present invention can provide a pemetrexed formulation which is easy to prepare in commercial manner, can be prevented from microbial contamination likely to occur during lyophilization and reconstruction, and has improved convenience and stability. In addition, the present invention can provide a stabilized pemetrexed formulation which contains acetylcysteine as antioxidant together with sodium citrate as buffer, and thereby exhibits no abnormalities in the appearance, such as discoloration or precipitation, and satisfies the acceptance criteria, unlike conventional pemetrexed-containing injectable liquid formulations.

BRIEF DESCRIPTION OF DRAWINGS

FIG. 1 shows a comparison of the appearance between conventional pemetrexed-containing injectable liquid formulations (Comparative Examples 1, 12 and 14) and the pemetrexed-containing injectable liquid formulation according to the present invention (Example 11) after a 4-week stress stability test (60° C. and 80%). For comparison, the appearance of WFI (water for injection) is also shown in FIG. 1.

BEST MODE FOR CARRYING OUT THE INVENTION

In one aspect, the present invention provides a pemetrexed formulation comprising: pemetrexed or a pharmaceutically acceptable salt thereof as an active ingredient; N-acetyl-L-cysteine; and a citrate salt.

In the present invention, the pemetrexed or a pharmaceutically acceptable salt thereof, the N-acetyl-L-cysteine and the citrate salt may be present at a concentration ratio of 1-30:0.15-2.0:1.0-15.0.

Preferably, the pemetrexed or a pharmaceutically acceptable salt thereof, the N-acetyl-L-cysteine and the citrate salt may be present at a concentration ratio of 1-30:1.5:1.0-15.0.

In the present invention, the formulation may be a liquid formulation storable in a solution state.

In the present invention, the formulation may be an injectable liquid formulation contained in a sealed container so as to be ready to use.

However, the scope of the present invention is not necessarily limited to an injectable liquid formulation and includes other liquid formulations and non-liquid formulations, which can be prepared according to common sense of those skilled in the art or according to methods that are generally used in the related technical field.

Hereinafter, the present invention will be described in detail.

Generally, a large variety of antioxidants are used for the purpose of stabilizing formulations, and specific examples thereof include parahydroxybenzoic acid ester derivatives, alcohols, phenol derivatives, thimerosal, acetic anhydride, sodium carboxylate, lauryl sulfate, antioxidants, sulfide compounds, sulfite, cystine, cystein, cysteamine, amino acids, organic acids such as ascorbic acid, retinol, tocopherol, butylated hydroxyanisole, etc.

In addition, Korean Patent Registration No. 10-0774366 discloses N-acetyl amino acid as antioxidant for paclitaxel, and Korean Patent Publication No. 10-2007-0028331 discloses monothioglycerol and ethylenediaminetetraacetic acid as antioxidants for diclofenac compositions.

The present inventors tested with the above-described antioxidants in injectable pemetrexed formulations, but daily doses of such commonly used substances are limited when used as excipients (antioxidants), not as APIs, particularly in injectable formulations. In addition, the antioxidants alone did not improve the stability of the formulations. Further, when ascorbic acid, lactic acid and the like that are frequently used in conventional injectable formulations were used, these injectable formulations partially discolored and/or generated precipitation, indicating that these formulations are acid-unstable (Experimental Examples 1 and 2).

However, the present inventors have surprisingly found that, when a composition comprising pemetrexed or a pharmaceutically acceptable salt thereof as an active ingredient was used together with acetylcysteine and sodium citrate, the active ingredient was not substantially modified during a 4-week stability test period under stress testing conditions (60° C. and 80%) and no discoloration or precipitation was occurred, indicating that the composition has stability that satisfies the required acceptance criteria (Experimental Examples 1 and 2). Acetylcysteine and sodium citrate are all substances that are generally used and are also advantageous in commercial terms due to their low price.

The pemetrexed formulation of the present invention comprises pemetrexed or a pharmaceutically acceptable salt thereof as an active ingredient. Said pemetrexed according to the present invention includes a pharmaceutically active drug or a drug that becomes pharmacologically active by an in vivo chemical or enzymatic process. Specifically, the pemetrexed that is used in the present invention may be the pemetrexed drug itself or a pharmaceutically acceptable salt thereof.

As used herein, the term "pemetrexed" refers to a compound named 5-substituted pyrrolo[2,3-d]pyrimidine. Specifically, the term refers to a multitargeted antifolate that is represented by the following formula 1 and exhibits anticancer effects against various cancers, including non-small cell lung cancer and malignant pleural mesothelioma:

Formula 1

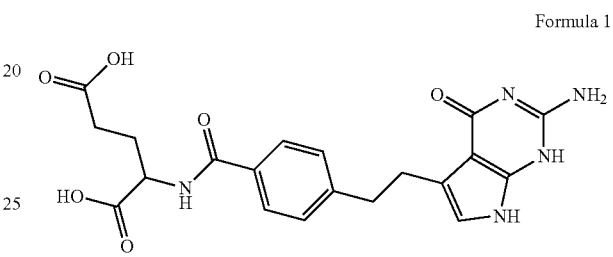

The pemetrexed exhibits anticancer effects against various cancers, including non-small cell lung cancer and malignant pleural mesothelioma, by inhibiting the activity of metabolites that are involved in folate metabolism.

As used herein, the term "pharmaceutically acceptable salt" refers to a salt prepared according to a conventional method known in the art. This preparation method is known to those skilled in the art. Specific examples of the pharmaceutically acceptable salt include, but are not limited to, salts derived from pharmacologically or physiologically acceptable inorganic acids, organic acids and bases as described below. Examples of suitable acids include hydrochloric acid, bromic acid, hydrobromide, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzene sulfonic acid, etc. Examples of salts derived from suitable bases include, but are not limited to, salts of alkali metals such as sodium and potassium, and salts of alkali earth metals such as magnesium.

As used herein, the term "acetylcysteine" refers to a compound named N-acetyl-L-cysteine (NAC, $C_5H_9NO_3S$, CAS number 616-91-1), which is used as antioxidant in the pemetrexed formulation of the present invention. In the present invention, "acetylcysteine" and "N-acetyl-L-cysteine" are used interchangeably with each other.

Acetylcysteine as antioxidant is described in the United States Pharmacopeia (see U.S. Pharmacopeia 35—National Formulary 10, p 2069). Acetylcysteine is a precursor of the amino acid L-cysteine contained in foods. Cysteine is easily changed into an insoluble substance by oxidization, whereas acetylcysteine is stable and does not change easily, so as to be administered orally or intravenously.

As used herein, the term "citrate salt" refers to a salt of citric acid and means a compound that is used as buffer in the pemetrexed formulation of the present invention. The citrate salt may be sodium citrate.

According to the present invention, a pemetrexed formulation that enables pemetrexed to be pharmaceutically stored in a stable manner at a temperature of 1 to 30° C. for a long period of time can be provided by using acetylcysteine as antioxidant together with sodium citrate as buffer.

In the pemetrexed formulation of the present invention, the concentration ratio of pemetrexed or a pharmaceutically acceptable salt thereof:N-acetyl-L-cysteine:citrate salt is preferably 1-30:0.15-2.0:1.0-15.0, and more preferably 1-30:1.5:1.0-15.0. Herein, each of the concentrations may be given in the unit of mg/mL. It could be seen that, in the case of pemetrexed formulations having concentration ratios out of the above concentration ratio range, the generation of impurities increased beyond the acceptance criteria with the passage of storage time (Experimental Example 1).

In the present invention, the pemetrexed formulation may comprise a pharmaceutically acceptable carrier and a pH-adjusting agent.

In the present invention, the pemetrexed formulation may preferably be a liquid formulation storable in solution state, and more preferably an injectable liquid formulation contained in a sealed container so as to be ready to use.

When the pemetrexed formulation of the present invention is an injectable liquid formulation, the pharmaceutically acceptable carrier is WFI (water for injection).

In the present invention, the pH of the injectable liquid formulation of pemetrexed may preferably be about 6.0-8.0, and more preferably about 7.2-7.8. The pH of the liquid formulation can be adjusted using acids such as hydrochloric acid, or bases such as sodium hydroxide.

While it is possible that the pemetrexed formulation of the present invention may comprise no other additives than acetylcysteine and citrate salts, it may further comprise a pharmaceutically acceptable excipient. Examples of the pharmaceutically acceptable excipient include known additives, such as lactose, dextrose, cyclodextrin and its derivatives, sucrose, glycerol, sodium carbonate. Preferred excipients may be sodium chloride and mannitol.

In a process of preparing the formulation of the present invention, purging with inert gas such as nitrogen or argon is performed in order to maintain low-oxygen condition, followed by sterilization and filtration.

In addition, the stabilized pemetrexed formulation of the present invention may be packed in an appropriate container known in the art. For example, the container may be a glass vial, a glass bottle, a cartridge, a pre-filled syringe or the like. Preferably, the container is a glass vial.

The injectable liquid formulation of pemetrexed according to the present invention is dispensed in a previously washed and sterilized container, and the container is sealed with a Teflon stopper whose surface is not reactive with the liquid formulation. If necessary, the space between the injectable liquid formulation and the stopper is filled with inert gas. The stopper is attached using a crimper, and then if necessary, the vial filled with the injectable liquid formulation is heated and sterilized.

MODE FOR THE INVENTION

Hereinafter, the present invention will be described in further detail with reference to examples. It is to be understood, however, that these examples are for illustrative purposes only and are not intended to limit the scope of the present invention.

Examples 1 to 14

Preparation of Pemetrexed-Containing Injectable Solutions Containing Different Amounts of Acetylcysteine as Antioxidant and Sodium Citrate as Buffer 2.5 g of D-mannitol was dissolved in 100 ml of WFI (water for injection), and then acetylcysteine and sodium citrate were sequentially added thereto at the concentrations shown in Table 1 below and were completely dissolved therein. 2.5 g of pemetrexed was slowly added to the solutions (3.0 g of pemetrexed was slowly added in Example 14), and the solutions were agitated until they became clear. Then, the solutions were adjusted to the pHs shown in Table 1 using an aqueous solution of hydrochloric acid or sodium hydroxide. The solutions were aseptically filtered through a sterilized 0.22-μm membrane filter in the clean room. The obtained solutions were filled into washed/sterilized sealable containers which were previously purged with nitrogen.

The components and pHs of the obtained pemetrexed-containing injectable solutions are shown in Table 1 below.

TABLE 1

| | Concentration (mg/mL) of active ingredient | Antioxidant | Concentration (mg/mL) of antioxidant | Buffer | Concentration (mg/mL) of buffer | pH |
| --- | --- | --- | --- | --- | --- | --- |
| Example 1 | 25 | Acetylcysteine | 0.15 | Sodium citrate | 2.0 | 7.3 |
| Example 2 | 25 | Acetylcysteine | 0.3 | Sodium citrate | 2.0 | 7.2 |
| Example 3 | 25 | Acetylcysteine | 0.5 | Sodium citrate | 1.0 | 7.2 |
| Example 4 | 25 | Acetylcysteine | 0.5 | Sodium citrate | 2.0 | 7.2 |
| Example 5 | 25 | Acetylcysteine | 0.5 | Sodium citrate | 3.0 | 7.3 |
| Example 6 | 25 | Acetylcysteine | 0.5 | Sodium citrate | 4.0 | 7.4 |
| Example 7 | 25 | Acetylcysteine | 0.5 | Sodium citrate | 5.0 | 7.4 |
| Example 8 | 25 | Acetylcysteine | 1.0 | Sodium citrate | 2.0 | 7.4 |
| Example 9 | 25 | Acetylcysteine | 1.5 | Sodium citrate | 1.0 | 7.5 |
| Example 10 | 25 | Acetylcysteine | 1.5 | Sodium citrate | 2.0 | 7.5 |
| Example 11 | 25 | Acetylcysteine | 1.5 | Sodium citrate | 5.0 | 7.5 |
| Example 12 | 25 | Acetylcysteine | 1.5 | Sodium citrate | 15.0 | 7.5 |
| Example 13 | 25 | Acetylcysteine | 2.0 | Sodium citrate | 5.0 | 7.4 |
| Example 14 | 30 | Acetylcysteine | 1.5 | Sodium citrate | 5.0 | 7.4 |

Examples 15 and 16

Preparation of Pemetrexed-Containing Injectable Solutions Having Different pHs 2.5 g of D-mannitol was dissolved in 100 ml of WFI (water for injection), and then acetylcysteine and sodium citrate were sequentially added thereto at the concentrations shown in Table 2 below and were completely dissolved therein. 2.5 g of pemetrexed was slowly added to the solutions, and the solutions were agitated until they became clear. Then, the solutions were adjusted to the pHs shown in Table 2 using an aqueous solution of hydrochloric acid or sodium hydroxide. The solutions were aseptically filtered through a sterilized 0.22-µm membrane filter in a clean room. The obtained solutions were filled into washed/sterilized sealable containers which were previously purged with nitrogen.

The components and pHs of the obtained pemetrexed-containing injectable solutions are shown in Table 2 below.

TABLE 2

|  | Concentration (mg/mL) of active ingredient | Antioxidant | Concentration (M) of antioxidant | Buffer | Concentration (mg/mL) of buffer | pH |
|---|---|---|---|---|---|---|
| Example 15 | 25 | Acetylcysteine | 1.5 | Sodium citrate | 5.0 | 6.8 |
| Example 16 | 25 | Acetylcysteine | 1.5 | Sodium citrate | 5.0 | 7.2 |

Comparative Examples 1 to 8

Preparation of Pemetrexed-Containing Injectable Solutions Using Varying Kinds of Antioxidants According to the components and contents shown in TABLE 3 below, pemetrexed-containing solutions were prepared in the same manner as described in Example 1. In Comparative Example 1, a solution without an antioxidant and containing WFI (water for injection) only as a carrier was prepared.

TABLE 3

|  | Concentration (mg/mL) of active ingredient | Kind of antioxidant | Concentration (mg/mL) of antioxidant | pH |
|---|---|---|---|---|
| Comparative Example 1 | 25 | — | — | 7.5 |
| Comparative Example 2 | 25 | Ascorbic acid | 0.3 | 6.5 |
| Comparative Example 3 | 25 | Sodium thiosulfate | 0.3 | 7.5 |
| Comparative Example 4 | 25 | Butylated hydroxyanisole | 0.3 | 9.9 |
| Comparative Example 5 | 25 | Propyl gallate | 0.3 | 9.5 |
| Comparative Example 6 | 25 | EDTA | 0.3 | 6.8 |
| Comparative Example 7 | 25 | L-Cystine | 0.3 | 7.5 |
| Comparative Example 8 | 25 | L-Methionine | 0.3 | 7.4 |

Comparative Examples 9 to 14

Preparation of Pemetrexed-Containing Injectable Solutions Containing Different Kinds of Antioxidants and Containing or not Containing Buffer According to the components and contents shown in Table 4 below, pemetrexed-containing solutions were prepared in the same manner as described in Example 1.

TABLE 4

| | Concentration (mg/mL) of active ingredient | Kind of antioxidant | Concentration (mg/mL) of antioxidant | Buffer | Concentration (mg/mL) of buffer | pH |
|---|---|---|---|---|---|---|
| Comparative Example 9 | 25 | — | — | Sodium citrate | 1.5 | 7.4 |
| Comparative Example 10 | 25 | — | — | Sodium citrate | 2.0 | 7.3 |
| Comparative Example 11 | 25 | Acetylcysteine | 0.5 | — | — | 7.2 |
| Comparative Example 12 | 25 | Acetylcysteine | 1.5 | — | — | 7.5 |
| Comparative Example 13 | 25 | L-cysteine | 0.5 | — | — | 7.5 |
| Comparative Example 14 | 25 | L-cysteine | 1.5 | — | — | 7.5 |

Comparative Examples 15 to 17

Preparation of Pemetrexed-Containing Injectable Solutions Containing Different Kinds of Buffers According to the components and contents shown in Table 5 below, pemetrexed-containing solutions were prepared in the same manner as described in Example 1.

TABLE 5

| | Concentration (mg/mL) of active ingredient | Kind of antioxidant | Concentration (mg/mL) of antioxidant | Buffer | Concentration (mg/mL) of buffer | pH |
|---|---|---|---|---|---|---|
| Comparative Example 15 | 25 | Acetylcysteine | 1.5 | Sodium acetate | 5.0 | 7.4 |
| Comparative Example 16 | 25 | Acetylcysteine | 1.5 | Sodium hydrogen phosphate | 5.0 | 7.5 |
| Comparative Example 17 | 25 | Acetylcysteine | 1.5 | Potassium dihydrogen phosphate | 5.0 | 7.5 |

Experimental Examples

Stability Test

The compositions prepared in Examples 1 to 16 and Comparative Examples 1 to 17 were tested for their stability under stress testing conditions (60° C. and 80%) for 4 weeks. Among these compositions, the compositions of Example 11 and Comparative Examples 1, 12 and 14 were also tested for their stability under accelerated conditions (40° C. and 70%) for 4 months. Stability evaluation was performed by measuring the contents of pemetrexed and impurities in aqueous solutions using high-performance liquid chromatography under the conditions shown in Table 6 below.

TABLE 6

| Column | C8, 150 × 4.6 mm, 3.5 μm |
|---|---|
| Detector | UV spectrophotometer (250 nm) |
| Mobile phase | Gradient method |
| | Mobile phase A - acetic acid buffer:acetonitrile (97:3) |
| | Mobile phase B - acetic acid buffer:acetonitrile (87.5:12.5) |
| | Acetic acid buffer (0.03 mol/L, pH 5.5) - obtained by adding 3.4 mL of acetic acid (100%) to 2 L of water, stirring the solution and adjusting the solution to a pH of 5.5 with 50% sodium hydroxide |
| Flow rate | 1 mL/min |
| Column temperature | 35° C. |
| Analysis time | 55 min |

Experimental Example 1

Stress Stability Testing (60° C./80%, 4-Week Evaluation)

Stress stability testing was performed as described above, and the results of the test are shown in Tables 7 to 11 below.

Also, FIG. 1 shows a comparison of the appearance between the pemetrexed-containing injectable liquid formulation according to the present invention (Example 11) and the pemetrexed-containing injectable liquid formulations in the art (Comparative Examples 1, 12 and 14) during the 4-week stability test period under stress testing conditions (60° C. and 80%). For comparison, the appearance of WFI (water for injection) is also shown in FIG. 1.

TABLE 7

| | Concentration (mg/mL) of active ingredient | Antioxidant | Concentration (mg/mL) of antioxidant | Buffer | Concentration (mg/mL) of buffer | pH | | Impurity (%) Individual/total |
|---|---|---|---|---|---|---|---|---|
| Example 1 | 25 | Acetylcysteine | 0.15 | Sodium citrate | 2.0 | 7.3 | Initial | 0.05/0.1 (colorless and transparent) |
| | | | | | | | 2 weeks | 0.09/0.3 yellow) |
| | | | | | | | 4 weeks | 0.11/0.6 (yellow) |
| Example 2 | 25 | Acetylcysteine | 0.3 | Sodium citrate | 2.0 | 7.2 | Initial | 0.07/0.1 (colorless and transparent) |
| | | | | | | | 2 weeks | 0.10/0.3 (pale yellow) |
| | | | | | | | 4 weeks | 0.12/0.6 (yellow) |
| Example 3 | 25 | Acetylcysteine | 0.5 | Sodium citrate | 1.0 | 7.2 | Initial | 0.07/0.1 (colorless and transparent) |
| | | | | | | | 2 weeks | 0.10/0.1 (light pale yellow) |
| | | | | | | | 4 weeks | 0.11/0.4 (pale yellow) |
| Example 4 | 25 | Acetylcysteine | 0.5 | Sodium citrate | 2.0 | 7.2 | Initial | 0.07/0.1 (colorless and transparent) |
| | | | | | | | 2 weeks | 0.10/0.1 (pale yellow) |
| | | | | | | | 4 weeks | 0.13/0.5 (pale yellow) |
| Example 5 | 25 | Acetylcysteine | 0.5 | Sodium citrate | 3.0 | 7.3 | Initial | 0.07/0.1 (colorless and transparent) |
| | | | | | | | 2 weeks | 0.15/0.3 (pale yellow) |
| | | | | | | | 4 weeks | 0.10/0.4 (pale yellow) |
| Example 6 | 25 | Acetylcysteine | 0.5 | Sodium citrate | 4.0 | 7.4 | Initial | 0.07/0.1 (colorless and transparent) |
| | | | | | | | 2 weeks | 0.10/0.2 (colorless and transparent) |
| | | | | | | | 4 weeks | 0.12/0.5 (pale yellow) |
| Example 7 | 25 | Acetylcysteine | 0.5 | Sodium citrate | 5.0 | 7.4 | Initial | 0.07/0.1 (colorless and transparent) |
| | | | | | | | 2 weeks | 0.10/0.2 (colorless and transparent) |
| | | | | | | | 4 weeks | 0.12/0.5 (pale yellow) |
| Example 8 | 25 | Acetylcysteine | 1.0 | Sodium citrate | 2.0 | 7.4 | Initial | 0.08/0.1 (colorless and transparent) |
| | | | | | | | 2 weeks | 0.11/0.2 (colorless and transparent) |
| | | | | | | | 4 weeks | 0.13/0.5 (colorless and transparent) |
| Example 9 | 25 | Acetylcysteine | 1.5 | Sodium citrate | 1.0 | 7.5 | Initial | 0.08/0.1 (colorless and transparent) |
| | | | | | | | 2 weeks | 0.11/0.2 (colorless and transparent) |
| | | | | | | | 4 weeks | 0.10/0.3 (colorless and transparent) |
| Example 10 | 25 | Acetylcysteine | 1.5 | Sodium citrate | 2.0 | 7.5 | Initial | 0.08/0.1 (colorless and transparent) |
| | | | | | | | 2 weeks | 0.12/0.1 (colorless and transparent) |
| | | | | | | | 4 weeks | 0.12/0.3 (colorless and transparent) |
| Example 11 | 25 | Acetylcysteine | 1.5 | Sodium citrate | 5.0 | 7.5 | Initial | 0.07/0.1 (colorless and transparent) |
| | | | | | | | 2 weeks | 0.10/0.1 (colorless and transparent) |
| | | | | | | | 4 weeks | 0.11/0.2 (colorless and transparent) |
| Example 12 | 25 | Acetylcysteine | 1.5 | Sodium citrate | 15.0 | 7.5 | Initial | 0.07/0.1 (colorless and transparent) |
| | | | | | | | 2 weeks | 0.11/0.1 (colorless and transparent) |
| | | | | | | | 4 weeks | 0.11/0.2 (colorless and transparent) |
| Example 13 | 25 | Acetylcysteine | 2.0 | Sodium citrate | 5.0 | 7.4 | Initial | 0.20/0.2 (colorless and transparent) |
| | | | | | | | 2 weeks | 0.25/0.4 (light pale yellow) |
| | | | | | | | 4 weeks | 0.25/0.6 (light pale yellow) |
| Example 14 | 30 | Acetylcysteine | 1.5 | Sodium citrate | 5.0 | 7.5 | Initial | 0.11/0.1 (colorless and transparent) |
| | | | | | | | 2 weeks | 0.15/0.2 (colorless and transparent) |
| | | | | | | | 4 weeks | 0.15/0.3 (light pale yellow) |

As can be seen from the results in Table 7, the formulations containing 1.5 mg/mL of acetylcysteine as antioxidant together with 1-15 mg/mL of sodium citrate as buffer showed individual impurities content of 0.2% or less and a total impurity content of 1.0% or less during the 4-week stress testing conditions, indicating that these formulations have excellent stability (Examples 9 to 12).

In addition, the formulations containing 1.0-1.5 mg/mL of acetylcysteine and 2.0 mg/mL of sodium citrate as buffer showed individual impurities content of 0.2% or less and a total impurity content of 1.0% or less, indicating that these formulations have excellent stability (Examples 8 and 10). However, it was observed that, when the concentration of acetylcysteine was lower than 1.0-1.5 mg/mL, a change in the appearance (discoloration) occurred although the impurity content satisfied the acceptance criteria (Examples 1 to 2).

In addition, when the concentration of acetylcysteine was 2.0 mg/mL and the concentration of sodium citrate was 5.0 mg/mL, the impurity content satisfied the acceptance criteria, but a change in the appearance (discoloration) occurred (Example 13).

Moreover, when the concentration of acetylcysteine was 0.5 mg/mL and the concentration of sodium citrate was 1.0-5.0 mg/mL, the impurity content satisfied the acceptance criteria, but a change in the appearance (discoloration) occurred (Examples 3 to 7).

TABLE 8

| | Concentration (mg/mL) of active ingredient | Antioxidant | Concentration (mg/mL) of antioxidant | Buffer | Concentration (mg/mL) of buffer | pH | | Impurity (%) Individual/total |
|---|---|---|---|---|---|---|---|---|
| Example 15 | 25 | Acetylcysteine | 1.5 | Sodium citrate | 5.0 | 6.9 | Initial | 0.16/0.2 (colorless and transparent) |
| | | | | | | | 2 weeks | 0.18/0.2 (colorless and transparent) |
| | | | | | | | 4 weeks | 0.17/0.3 (colorless and transparent) |
| Example 16 | 25 | Acetylcysteine | 1.5 | Sodium citrate | 5.0 | 7.2 | Initial | 0.14/0.2 (colorless and transparent) |
| | | | | | | | 2 weeks | 0.15/0.3 (colorless and transparent) |
| | | | | | | | 4 weeks | 0.14/0.2 (colorless and transparent) |
| Example 11 | 25 | Acetylcysteine | 1.5 | Sodium citrate | 5.0 | 7.5 | Initial | 0.07/0.1 (colorless and transparent) |
| | | | | | | | 2 weeks | 0.10/0.1 (colorless and transparent) |
| | | | | | | | 4 weeks | 0.11/0.2 (colorless and transparent) |

As can be seen from the results in Table 8 above, the formulations containing acetylcysteine as antioxidant together with sodium citrate as buffer showed individual impurities content of 0.2% or less and a total impurity content of 1.0% or less during the 4-week stability test period under stress conditions despite the changes in the pH, indicating these formulations have excellent stability.

TABLE 9

| | Concentration (mg/mL) of active ingredient | Kind of antioxidant | Concentration (mg/mL) of antioxidant | pH | | Impurity (%) Individual/total |
|---|---|---|---|---|---|---|
| Comparative Example 1 | 25 | — | — | 7.5 | Initial | 0.01/0.1 |
| | | | | | 2 weeks | 0.33/0.8 |
| | | | | | 4 weeks | 0.66/2.1 |
| Comparative Example 2 | 25 | Ascorbic acid | 0.3 | 6.5 | Initial | 0.63/0.7 |
| | | | | | 2 weeks | 0.6/1.0 |
| | | | | | 4 weeks | N.A. (appearance unsatisfied) |
| Comparative Example 3 | 25 | Sodium thiosulfate | 0.3 | 7.5 | Initial | 0.04/0.2 |
| | | | | | 2 weeks | 0.24/0.6 |
| | | | | | 4 weeks | 0.72/1.7 |
| Comparative Example 4 | 25 | Butylated hydroxyanisole | 0.3 | 9.9 | Initial | 0.1/0.3 |
| | | | | | 2 weeks | 0.45/1.3 |
| | | | | | 4 weeks | N.A. (appearance unsatisfied) |
| Comparative Example 5 | 25 | Propyl gallate | 0.3 | 9.5 | Initial | 0.11/0.4 |
| | | | | | 2 weeks | 1.03/2.7 |
| | | | | | 4 weeks | N.A. (appearance unsatisfied) |

TABLE 9-continued

|  | Concentration (mg/mL) of active ingredient | Kind of antioxidant | Concentration (mg/mL) of antioxidant | pH |  | Impurity (%) Individual/total |
|---|---|---|---|---|---|---|
| Comparative Example 6 | 25 | EDTA | 0.3 | 6.5 | Initial<br>2 weeks<br>4 weeks | 0.53/2.7<br>1.23/3.0<br>N.A. (appearance unsatisfied) |
| Comparative Example 7 | 25 | L-cystine | 0.3 | 7.5 | Initial<br>2 weeks<br>4 weeks | 0.05/0.2<br>0.38/1.0<br>0.71/1.8 |
| Comparative Example 8 | 25 | L-methionine | 0.3 | 7.4 | Initial<br>2 weeks<br>4 weeks | 0.05/0.2<br>0.35/0.9<br>0.51/1.3 |

As can be seen from the results in Table 9 above, in the formulations containing the antioxidants that are generally used in the art, the change in the appearance (precipitation or discoloration) occurred during the stability test period under stress conditions, or the content of individual impurity increased to higher than 0.2% and the total impurity content increased to higher than 1.0%. This shows that pemetrexed-containing injectable solutions containing the antioxidants that are generally used in the art do not provide sufficient stability in terms of impurities or a change in the appearance.

TABLE 10

|  | Concentration (mg/mL) of active ingredient | Kind of antioxidant | Concentration (mg/mL) of antioxidant | Buffer | Concentration (mg/mL) of buffer | pH |  | Impurity (%) Individual/total |
|---|---|---|---|---|---|---|---|---|
| Comparative Example 9 | 25 | — | — | Sodium citrate | 1.5 | 7.4<br>7.4<br>— | Initial<br>2 weeks<br>4 weeks | 0.15/0.2 (colorless and transparent)<br>0.13/0.6 (deep yellow)<br>N.A. (appearance unsatisfied) |
| Comparative Example 10 | 25 | — | — | Sodium citrate | 2.0 | 7.3<br>7.0<br>7.0 | Initial<br>2 weeks<br>4 weeks | 0.03/0.0 (colorless and transparent)<br>0.11/0.3 (deep yellow)<br>0.17/0.5 (deep yellow) |
| Example 11 | 25 | Acetylcysteine | 1.5 | Sodium citrate | 5.0 | 7.5<br>7.3<br>7.2 | Initial<br>2 weeks<br>4 weeks | 0.07/0.1 (colorless and transparent)<br>0.10/0.1 (colorless and transparent)<br>0.11/0.2 (colorless and transparent) |
| Comparative Example 11 | 25 | Acetylcysteine | 0.5 | — | — | 7.2<br>6.9<br>6.9 | Initial<br>2 weeks<br>4 weeks | 0.12/0.1 (colorless and transparent)<br>0.14/0.3 (pale yellow)<br>0.15/0.5 (pale yellow) |
| Example 8 | 25 | Acetylcysteine | 0.5 | Sodium citrate | 5.0 | 7.4<br>7.1<br>7.1 | Initial<br>2 weeks<br>4 weeks | 0.07/0.1 (colorless and transparent)<br>0.10/0.2 (colorless and transparent)<br>0.12/0.5 (pale yellow) |
| Comparative Example 12 | 25 | Acetylcysteine | 1.5 | — | — | 7.5<br>7.1<br>7.0 | Initial<br>2 weeks<br>4 weeks | 0.09/0.1 (colorless and transparent)<br>0.12/0.3 (colorless and transparent)<br>0.12/0.3 (light pale yellow) |

TABLE 10-continued

| | Concentration (mg/mL) of active ingredient | Kind of antioxidant | Concentration (mg/mL) of antioxidant | Buffer | Concentration (mg/mL) of buffer | pH | | Impurity (%) Individual/total |
|---|---|---|---|---|---|---|---|---|
| Comparative Example 13 | 25 | L-cysteine | 0.5 | — | — | 7.5 | Initial | 0.12/0.2 (colorless and transparent) |
| | | | | | | 6.9 | 2 weeks | 0.12/0.2 (pale yellow and abnormal odor) |
| | | | | | | 6.9 | 4 weeks | 0.12/0.3 (pale yellow) |
| Comparative Example 14 | 25 | L-cysteine | 1.5 | — | — | 7.5 | Initial | 0.09/0.1 (colorless and transparent) |
| | | | | | | 7.4 | 2 weeks | 0.11/0.1 (abnormal odor) |
| | | | | | | 7.2 | 4 weeks | 0.12/0.2 (abnormal odor) |

As can be seen from the results in Table 10 above, when the formulation contained acetylcysteine as antioxidant together with sodium citrate as buffer, preferably when the concentration of acetylcysteine was 1.5 mg/mL and the concentration of sodium citrate was 5.0 mg/mL, the formulation showed individual impurities content of 0.2% or less and a total impurity content of 1.0% or less during the 4-week stability test period under stress conditions, indicating that this formulation has excellent stability (Example 11).

However, in the case in which the formulation solution contained only sodium citrate as buffer, it was clearly observed that the color of the solution began to change to deep yellow after 2 weeks under stress conditions (Comparative Examples 9 and 10). In addition, in the case in which the formulation contained L-cysteine or acetylcysteine as antioxidant, it was clearly observed that the color of the solution began to change to pale yellow after 2 weeks under stress conditions and that the pH significantly decreased during the 4-week test period under stress conditions (Comparative Examples 11 and 12 to 14). In other words, it was seen that the combined use of acetylcysteine and sodium citrate significantly improved the stability of impurities, unlike the use of acetylcysteine or sodium citrate alone.

In addition, it was shown that, in the formulation solutions of Comparative Examples 13 and 14, which contain only L-cysteine, an abnormal odor like a bad egg started to occur after 2 weeks under severe conditions, but in the formulation of the present invention, this abnormal odor did not occur.

TABLE 11

| | Concentration (mg/mL) of active ingredient | Kind of antioxidant | Concentration (mg/mL) of antioxidant | Buffer | Concentration (mg/mL) of buffer | pH | | Impurity (%) Individual/total |
|---|---|---|---|---|---|---|---|---|
| Example 11 | 25 | Acetylcysteine | 1.5 | Sodium citrate | 5.0 | 7.5 | Initial | 0.07/0.1 (colorless and transparent) |
| | | | | | | 7.3 | 2 weeks | 0.10/0.1 (colorless and transparent) |
| Comparative Example 15 | 25 | Acetylcysteine | 1.5 | Sodium acetate | 5.0 | 7.4 | Initial | 0.89/1.45 (pale yellow) |
| | | | | | | 7.1 | 2 weeks | 0.86/2.3 (deep yellow) |
| Comparative Example 16 | 25 | Acetylcysteine | 1.5 | Sodium hydrogen phosphate | 5.0 | 7.5 | Initial | 0.23/0.2 (colorless and transparent) |
| | | | | | | 7.4 | 2 weeks | 0.21/0.9 (yellow) |
| Comparative Example 17 | 25 | Acetylcysteine | 1.5 | Potassium dihydrogen phosphate | 5.0 | 7.5 | Initial | 0.24/0.2 (colorless and transparent) |
| | | | | | | 7.2 | 2 weeks | 0.23/0.8 (light pale yellow) |

As can be seen from the results in Table 11 above, the stabilities of the formulations containing acetylcysteine as antioxidant and various buffers that are generally used were compared, and, it was found that, when buffers other than sodium citrate were used, the change in the appearance (discoloration) occurred in the initial stage, or the individual impurity content increased to higher than 0.2% and the total impurity content increased to higher than 1.0%.

Thus, it was confirmed that only the pemetrexed-containing injectable solution containing acetylcysteine as antioxidant together with sodium citrate as buffer showed the best stability.

Experimental Example 2

Accelerated Stability Test (40° C./70%, 4-Month Evaluation)

Accelerated stability test was performed as described above, and the results of the test are shown in Table 12 below.

tion changed to yellow after 4 months under accelerated conditions, and the individual impurity content was more than 0.2%, indicating that the formulation has insufficient stability (Comparative Example 12).

In addition, in the case of the formulation of Comparative Example 14, which contains only L-cysteine, the contents of impurities satisfied the acceptance criterias, and an abnormal odor like a bad egg occurred, as in the results of the stress stability test. However, this abnormal odor did not occur in the formulation of the present invention, that is, in the formulation of Example 11.

The invention claimed is:

1. A pemetrexed formulation comprising: pemetrexed or a pharmaceutically acceptable salt thereof as an active ingredient; N-acetyl-L-cysteine; and a citrate salt.

2. The pemetrexed formulation of claim 1, wherein the concentration ratio of pemetrexed or a pharmaceutically acceptable salt thereof:the N-acetyl-L-cysteine:the citrate salt is 1-30:0.15-2.0:1.0-15.0.

TABLE 12

| | Concentration (mg/mL) of active ingredient | Kind of antioxidant | Concentration (mg/mL) of antioxidant | Buffer | Concentration (mg/mL) of buffer | pH | | Impurity (%) Individual/total |
|---|---|---|---|---|---|---|---|---|
| Example 11 | 25 | Acetylcysteine | 1.5 | Sodium citrate | 5.0 | 7.5 | Initial | 0.07/0.1 (colorless and transparent) |
| | | | | | | 7.3 | 2 months | 0.10/0.1 (colorless and transparent) |
| | | | | | | 7.3 | 4 months | 0.14/0.2 (colorless and transparent) |
| | | | | | | 7.2 | 6 months | 0.18/0.4 (light pale yellow) |
| Comparative Example 1 | 25 | — | — | — | — | 7.5 | Initial | 0.01/0.1 |
| | | | | | | — | 2 months | 0.04/0.1 (yellow) |
| | | | | | | — | 4 months | 0.60/1.5 (yellow) |
| Comparative Example 12 | 25 | Acetylcysteine | 1.5 | — | — | 7.5 | Initial | 0.09/0.1 (colorless and transparent) |
| | | | | | | 7.1 | 4 months | 0.33/0.8 (colorless and transparent) |
| Comparative Example 14 | 25 | L-cysteine | 1.5 | — | — | 7.5 | Initial | 0.09/0.1 (colorless and transparent) |
| | | | | | | 7.2 | 4 months | 0.12/0.2 (colorless, transparent, and abnormal odor) |

As can be seen from the results in Table 12 above, in the formulation of Comparative Example 1, which was prepared using only WFI (water for injection) as a carrier without adding an antioxidant, the appearance of the solution changed to yellow after 2 months under accelerated conditions, and the solution showed individual impurities content of 0.2% or more and a total impurity content of 1% at 4 months, indicating that the formulation has insufficient stability. Meanwhile, in the formulation of Example 11 which contained acetylcysteine as antioxidant together with sodium citrate as buffer, showed individual impurities content of 0.2% or less and a total impurity content of 1.0% or less during the 6-month test period under accelerated conditions, indicating that the formulation has excellent stability.

By contrast, it was found that, in the formulation containing only acetylcysteine as antioxidant, the color of the solu- 3. The pemetrexed formulation of claim 2, wherein the concentration ratio of pemetrexed or a pharmaceutically acceptable salt thereof:the N-acetyl-L-cysteine:the citrate salt is 1-30:1.5:1.0-15.0.

4. The pemetrexed formulation of claim 1, wherein the citrate salt is sodium citrate.

5. The pemetrexed formulation of claim 1, wherein the formulation is a liquid formulation storable in a solution state.

6. The pemetrexed formulation of claim 1, wherein the formulation is an injectable liquid formulation contained in a sealed container so as to be ready to use.

* * * * *